United States Patent [19]

Deavenport et al.

[11] Patent Number: 5,206,401

[45] Date of Patent: * Apr. 27, 1993

[54] METHOD OF MAKING ALKYLALUMINOXANE

[75] Inventors: Dennis L. Deavenport, Seabrook; James T. Hodges, III, Alvin, both of Tex.; Dennis B. Malpass, Peekskill, N.Y.; Nam H. Tran, Houston, Tex.

[73] Assignee: Akzo Chemicals Inc., Chicago, Ill.

[*] Notice: The portion of the term of this patent subsequent to Aug. 20, 2008 has been disclaimed.

[21] Appl. No.: 712,310

[22] Filed: Jun. 7, 1991

Related U.S. Application Data

[63] Continuation-in-part of Ser. No. 534,913, Jun. 8, 1990, Pat. No. 5,041,585, Ser. No. 560,952, Aug. 1, 1990, Pat. No. 5,041,584, and Ser. No. 560,953, Aug. 1, 1990, Pat. No. 5,086,024.

[51] Int. Cl.$^5$ ............................................. C07F 5/06
[52] U.S. Cl. ................................... 556/175; 556/179; 556/187
[58] Field of Search ........................ 556/179, 175, 187

[56] References Cited

U.S. PATENT DOCUMENTS

| | | | |
|---|---|---|---|
| 3,300,458 | 1/1967 | Deavenport et al. | 556/179 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,908,463 | 3/1990 | Bottelberghe | 556/179 |
| 4,924,018 | 5/1990 | Bottelberghe | 556/179 |
| 4,937,363 | 1/1990 | Smith, Jr. et al. | 556/179 |
| 4,960,878 | 10/1990 | Crapo et al. | 556/179 |
| 4,968,827 | 11/1990 | Davis | 556/179 |
| 5,003,095 | 3/1991 | Beard | 556/179 |
| 5,041,585 | 8/1991 | Deavenport et al. | 556/179 |

*Primary Examiner*—José G. Dees
*Assistant Examiner*—Porfirio Nazario-Gonzalez
*Attorney, Agent, or Firm*—Richard P. Fennelly; Louis A. Morris

[57] ABSTRACT

The efficient production of alkylaluminoxane by the reaction of water, e.g., in the form of atomized water, and trialkylaluminum, e.g., trimethylaluminum, in an organic solvent medium can be achieved using a preformed alkylaluminoxane as a reaction moderator in the reaction mixture.

10 Claims, No Drawings

METHOD OF MAKING ALKYLALUMINOXANE

This is a continuation-in-part of copending U.S. patent application Ser. No. 534,913, filed Jun. 8, 1990, now U.S. Pat. No. 5,041,585, of U.S. Patent application Ser. No. 560,952, filed Aug. 1, 1990, and of U.S. patent application Ser. No. 560,953, filed Aug. 1, 1990, now U.S. Pat. No. 5,086,024.

BACKGROUND OF THE INVENTION

Alkylaluminoxane, e.g., methylaluminoxane, is made by the reaction of a trialkylaluminum, e.g., trimethylaluminum, with water in an organic solvent medium which is inert to the reaction. Since the reaction between water and a trialkylaluminum compound, particularly trimethylaluminum, is highly exothermic and quite difficult to control, investigators have used a wide variety of differing techniques to achieve a controllable reaction of these reagents in order to synthesize the desired alkylaluminoxane which is useful as a co-catalyst for olefin polymerization reactions with certain metallocene components, e.g., certain Group IVB compounds such as dicyclopentadienylzirconium dichloride. Some U.S. Pat. Nos. which are considered germane to this area of technology and which illustrate various specific techniques that have been used to combine liquid water and a trialkylaluminum reagent in aluminoxane synthesis are the following: U.S. Pat. Nos. 3,300,458; 4,730,071; 4,730,072; 4,772,736; 4,908,463; 4,924,018; 4,937,363; and 4,968,827.

U.S. Pat. No. 4,960,878 describes the synthesis of "modified" methylaluminoxane materials using various process embodiments. One embodiment, i.e., the third enumerated embodiment, involves the initial synthesis of a polyalkylaluminoxane containing $C_2$ or higher hydrocarbyl (e.g., alkyl) groups with the subsequent reaction of this polyalkylaluminoxane with trimethylaluminum and then with water. The trimethylaluminum is said in that patent to complex with the polyalkylaluminoxane prior to subsequent reaction with water (Col. 3, lines 49–52).

Recent U.S. Pat. No. 5,003,095 relates to the reaction of a methyl halide using a bismuth-containing catalyst with an alkylaluminoxane having two or more carbons via alkyl group exchange to form methylaluminoxane.

One very efficient way in which liquid water and trialkylaluminoxane can be combined in an alkylaluminoxane synthesis procedure is described in copending U.S. patent application Ser. No. 534,913, filed Jun. 8, 1990 in which atomized liquid water in the form of a spray, mist, or fog and the selected trialkylaluminum compound are combined in an organic solvent of the type used in conventional synthesis procedures for alkylaluminoxane synthesis.

SUMMARY OF THE INVENTION

It has now been found that alkylaluminoxane production by the reaction, in an inert organic solvent medium, of liquid water and a trialkylaluminum reagent can be improved by using a preformed aluminoxane as a reaction moderator. In particular, practice of this invention allows for the production of polyalkylaluminoxanes in high yields and high final concentrations without the use of complex equipment, exotic raw materials, or unusual process conditions (e.g., temperatures, intense agitation, etc.).

DETAILED DESCRIPTION OF THE INVENTION

The present invention reacts a trialkylaluminum reagent with water in a controlled manner using a preformed aluminoxane as a reaction moderator, in an organic solvent medium, to achieve the production of an aluminoxane product. It is well known that the aluminoxane produced by such a reaction is useful as a component in polymerization and oligomerization catalysts These aluminoxanes, as is also well known, can be cyclic, linear, or branched The trialkylaluminum reagents (e.g., the $C_1$–$C_{12}$ trialkylaluminum species) useful herein are known in the art as suitable for producing aluminoxanes upon appropriate reaction with water. Representative examples of such reagents include trimethylaluminum (the preferred reagent), triethylaluminum, triisopropylaluminum, tri-n-propylaluminum, triisobutylaluminum, tri-n-pentylaluminum, and the like. Mixtures of such reagents may also be used, if desired.

The organic solvent medium used in accordance with the present invention is one which provides good solvency and is substantially inert (e.g., is non-oxygenated, non-protic so as not to react or form strong complexes) to the trialkylaluminum starting material and the final aluminoxane product. Examples of such organic solvents include the saturated aliphatic solvents, the cycloaliphatics, and the aromatic solvents such as described in U.S. Pat. No. 4,730,071, for example.

The reaction temperature is advantageously kept below about 10° C., preferably below 0° C, e.g., $-5°$ C. to $-10°$ C. In general, the longer the alkyl chain on the selected trialkylaluminum reagent, the higher can be the selected temperature. Pressure is not critical The process does not require complex process equipment or exotic raw materials (such as hydrated salts as a source of the water reagent).

The invention, in its preferred embodiment, depends upon the atomization of a stream of water and the feeding of the atomized spray to the solution containing the trialkylaluminum reagent which is to be hydrolyzed to form the aluminoxane. The use of atomized water (e.g., in the form of a fog, mist, or spray) especially when delivered subsurface to the solution, as is preferred, obviates the need to mechanically disperse the water in the solvent medium by either rapid stirring, ultrasonic vibrational energy, static mixing or the like to the degree taught in U.S. Pat. Nos. 4,730,071, 4,730,072, 4,772,736 or 4,908,463. However, it is within the scope of the present invention to utilize other means for bringing liquid water in contact with the trialkylaluminum reagent, in the organic solvent which contains the aluminoxane reaction moderator, including using the techniques taught by the aforementioned patents.

The present invention is dependent upon the finding that the presence of a preformed alkylaluminoxane in the reaction mixture when the trialkylaluminum and liquid water are reacted serves as a reaction moderator and allows for the rapid and controlled production of an alkylaluminoxane having good properties as a co-catalyst.

The terminology "reaction moderator" as used herein is meant to indicate that in some manner the preformed aluminoxane allows for the conducting of the reaction between liquid water and trialkylaluminum reagent at respective concentrations of each that are higher than would be possible without the preformed aluminoxane with the "moderated" process nevertheless showing one or more of the following desired results: a high yield of aluminoxane product (e.g., 70%–90% as compared to the more conventional yields of 40%–60%); a generally low level of undesired solids formation; and/or a relatively high polymer activity for the aluminoxane (e.g., $1-2 \times 10^6$ g polyethylene/g zirconium.atm.hr). While the present inventors do not wish to be bound by the theoretical basis for the good results achievable with use of the present invention, it is believed that the preformed aluminoxane somehow complexes with at least a portion of the trialkylaluminum reagent thereby rendering it less reactive and less exothermic when reacted with the liquid water reagent. The net result is a more controlled reaction which gives good soluble yields of high activity aluminoxane with a relatively low level of undesired solids formation.

The instant invention, in one embodiment, allows for the direct production of polymethylaluminoxane (PMAO) at high concentrations (e.g., $\geq 10$ wt% aluminum in a two-stage process without the need for solvent evaporation to attain such high final PMAO concentrations This two-stage process can involve the initial combination of the trialkylaluminum and preformed aluminoxane, in suitable solvent medium, followed by the reaction with liquid water in a controlled manner at an initial water:trialkylaluminum molar ratio of 0.05 to 0.65, preferably 0.45–0.55, product therein. Then, the second stage of the reaction is conducted in which the resulting reaction mixture is contacted with additional water at a higher water:trialkylaluminum molar ratio in the range of 0.4–1.0, preferably 0.60–0.85.

The present invention, in another embodiment, also involves a "single-stage" process in which the water/trialkylaluminum (e.g., trimethylaluminum) reagent ratio is maintained at a selected final target ratio (e.g., about 0.65 to 0.8) throughout substantially the entire reaction by careful control of the amount of the two reagents until such final target ratio is achieved.

If desired, it is also within the contemplation of the present invention to initiate the instant process using a highly diluted trialkylaluminum-containing system rather than a preformed aluminoxane. The initial stages of the reaction would be conducted at concentrations less than about 3 wt% aluminum (preferably $\leq 1.5$ wt% aluminum) to form a dilute aluminoxane moderator in situ. As shown in Example 6, attempting to produce polymethylaluminoxane by direct addition of water to solutions of trimethylaluminum at molar ratios of above 1.5 is less controllable and results in progressively lower soluble yields. Then, after the aluminoxane has been formed in situ (so as to be "preformed" for later portions of the reaction), the water:trialkylaluminum ratio can be raised to the values mentioned before (e.g., 0.45–0.55 and then 0.60–0.85).

The one- and two-stage processes described above can be carried out in a batch type process. The two reaction stages can also be separated with either or both stages being carried out continuously or semi-continuously in reactors of the continuous stirred tank variety or of tubular design If desired, the trialkylaluminum and water reagents can be added to the reaction mixture sequentially or continuously.

The present invention is further illustrated by the Examples which follow.

A polymethylaluminoxane (PMAO) preparation run was conducted in a four-necked 1 liter round bottom reaction flask fitted with a condenser and a mechanical agitator A highly dilute solution of trimethylaluminum (15.6 g, 0.213 mole) in toluene (360 g), which contained about 1.5% aluminum, was prepared and was transferred to the reaction flask. The solution was then cooled down to $-10°$ C. Water (2.49 g, 0.138 mole) with a H$_2$O/Al molar ratio of 0.65 was introduced into the solution using a syringe with a 22 gauge needle to produce a dilute solution of preformed PMAO. Some solids formation was noted during this step. The reaction temperature was maintained between 5° C. to $-10°$ C. during the water addition. After the water charge was completed, trimethylaluminum (TMAL) was then added to the flask to increase the Al concentration by 1.5 wt%, and the corresponding amount of water was injected into the solution. This procedure was repeated for seven more additions. After completing the additions, the reaction mixture was heated to 55° C. and maintained at this temperature for an hour. Total amounts of 174.7 g (2.383 moles) TMAL and 27.88 g (I.549 moles) water were added to the reaction flask. The final PMAO solution was calculated to contain 12.53 wt% Al by theory. Actually, the analysis showed the material had 10.37 wt% soluble Al. The yield of soluble PMAO was calculated to be 78%. A polymerization test gave an activity of $1.2 \times 10^6$ g PE/(g Zr.atm.hr) at 80° C.

In the second Example, the conditions and quantities of starting materials were kept approximately the same as those in Example 1 except that water was introduced into the reactor mixture at a H$_2$O/Al molar ratio at 0.50 for each TMAL addition, and a final introduction was done to increase the overall ratio from 0.50 to 0.65. Total amounts of (173.7g, 2.36 moles) TMAL and (27.6 g, 1.53 moles) water were added to the flask containing 342 g toluene. Theoretically, the Al concentration of final solution should have been 12.87 wt%. Analysis indicated that the clear PMAO solution contained 10.62 wt% Al. The yield and polymerization activity at 80° C. of the material were 78% and $1.2 \times 10^6$ g PE/(g Zr.atm.hr), respectively.

EXAMPLE 3

This is a scale-up run conducted in a 10-gallon reactor using the same procedure for Example 1.

Toluene (21,200 g) and TMAL (1,058 g, 14.39 moles) were added to the reactor to form a dilute solution for preparation of preformed PMAO. With the agitation rate setting at 160 rpm, the contents were cooled down to $-10°$ C. An amount of water corresponding to an H$_2$O/Al molar ratio of 0.65 was introduced into the solution as an atomized water spray. With the maximum flow of refrigerating oil through the jacket of the reactor, the reactor temperature was maintained in the range of $-10°$ C. to 5° C. by adjusting the water flow rate. After completing the water injection, approximately the same amount of TMAL of the first charge was transferred to the reactor and a corresponding amount of water was fed to the reactor. This procedure was repeated for an additional eight times. After all the TMAL and water charges were completed, the reactor contents were heated and maintained at 55° C. for an hour. A total of 10,632 g (144.6 moles) of TMAL and 1,718 g (95.4 moles) of water were charged to the reactor. Analysis of the clear supernatant showed 10.92 wt% Al compared to the theoretical value of 12.80 wt% Al. The yield was calculated as 80.8%. The product showed a polymerization activity of $1.2 \times 10^6$ g PE/(g Zr.atm.hr) at 80° C. in homogeneous Ziegler catalysis.

EXAMPLE 4

This is a scale-up run conducted in a 10 gallon reactor using the procedure applying of Example 2. The reaction conditions and quantities of starting materials were kept approximately the same as those in Example 3.

| Toluene: | 21,200 g |
|---|---|
| TMAL: | 10,677 g (145.22 moles) |
| Water: | 1,707 g (94.83 moles) |
| $H_2O$/TMAL Ratio: | 0.653 |
| Theoretical wt % Al: | 12.83 |
| Actual wt % Al: | 11.50 |
| % Yield: | 86.3 |
| Activity: | $1.1 \times 10^6$ g PE/(g Zr.atm.hr) at 80° C. |

EXAMPLE 5

This represents a semi-continuous process in which TMAL/toluene and water, at a $H_2O$/TMAL molar ratio at 0.5, were added independently and continuously to a 10-gallon reactor with a heel of preformed methylaluminoxane solution in the reactor. The contents were subsequently heated and maintained at 55–60° C. for an hour. An additional amount of water was injected incrementally into the reactor at −10° C. to −5° C. to increase the ratio from 0.5 to 0.85. Samples were taken after heating the solution to 55–60° C. at ratios 0.65, 0.70, 0.75, 0.80 and 0.85. The data and results are summarized below:

| Toluene: | 14,500 g | |
|---|---|---|
| PMAO/Toluene Heel: | 2,785 g (contained 11.5 wt % Al) | |
| TMAL/Toluene: | 14,500 g (contained 3,678 g Al) | |
| Water Feed Rate: | 2.0 cc/min | |
| TMAL/Toluene Rate: | 24 g/min | |
| $H_2O$/Al Molar Ratio | % Yield ($Al_{SOLUBLE}$/$Al_{TOTAL}$) | Polymer Activity ($10^6$ g PE/g Zr.atm.hr) |
| 0.50 | 92.1 | 0.93 |
| 0.65 | 90.0 | 1.24 |
| 0.70 | 88.3 | 1.83 |
| 0.75 | 86.4 | 2.00 |
| 0.80 | 84.6 | 1.96 |
| 0.85 | 81.5 | 1.08 |

COMPARATIVE EXAMPLE 6

This is presented for comparative purposes to illustrate the inferior results obtained when relatively high aluminum concentrations in the TMAL solution were employed without preformed polymethylaluminoxane in the reaction medium.

A series of three experiments were conducted in four-necked 1 and 2 liter round-bottom reaction flasks fitted with condensers and mechanical agitators. The first reaction was run in 2-liter equipment starting with a 4% TMAL (29.5 g, 0.409 mole) solution in toluene (700.1 g). A total of 3.91 g $H_2O$ (0.217 mole) was added over a twenty-five minute interval starting at −15° C. and ending at −20° C. to give a final PMAO solution with a $H_2O$/TMAL molar ratio of 0.54. The solution was allowed to warm to 40° C. at which point agitation was stopped, and the solids were allowed to settle. The clear solution was then decanted, weighed and analyzed for aluminum content to determine actual recovered and calculated yields. Two additional runs at 8% and 12% initial TMAL concentrations were conducted in 1 liter flasks under similar conditions in order to demonstrate the influence of starting TMAL concentration on solids formation, PMAO yield (soluble) and process control. In the second run an 8% TMAL solution (34.5 g, 0.481 mole) in toluene (396.9 g was reacted with 4.40 g $H_2O$ (0.244 mole) to give a final PMAO solution with a $H_2O$/TMAL molar ratio of 0.51. In the third run a 12% TMAL solution (55.1 g, 0.764 mole) in toluene (403.3 g) was reacted with 6.79 g $H_2O$ (0.377 mole) to give a $H_2O$/TMAL molar ratio of 0.50. Higher concentrations were not attempted because of the extreme reactivity and difficulty in controlled the 12% TMAL reaction. The recovered yields for the 4%, 8% and 12% TMAL/toluene reactions decreased from 93% to 79% and, finally, to 66% with a noticeable increase in solids formation as the initial TMAL concentration was increased. Polymerization activities were not determined.

EXAMPLES 7-13

A series of seven pilot plant runs were conducted to produce product inventory for customer evaluation and to test the reproducibility of the process. The process conditions and stoichiometries were kept approximately the same as those in Example 5 except that a final molar ratio of $H_2O$/A = 0.75 was selected for the second stage. The overall stoichiometry consisted of 21 kg toluene, 10 kg TMAL, 712 g preformed PMAO and 1840 g $H_2O$ (1227 g for stage 1 and 613 g for stage 2 additions). The results are illustrated as follows:

| Pilot Plant Run No. | % Yield ($Al_{SOLUBLE}$/$Al_{TOTAL}$) | Polymer Activity ($10^6$ g PE/ g Zr.atm.hr) |
|---|---|---|
| 1 | 85.4 | 2.4 |
| 2 | 83.2 | 2.0 |
| 3 | 79.6 | 1.4 |
| 4 | 79.7 | 1.7 |
| Combined 1, 2, 3 & 4 | 2.1 | |
| 5 | 78.5 | 1.3 |
| 6 | 85.0 | 1.9 |
| 7 | 81.0 | 1.5 |
| Combined 5, 6 & 7 | 1.7 | |

The foregoing Examples have been provided to illustrate only certain embodiments of the present invention and should not be construed in a limiting sense for that reason. The scope of protection sought is set forth in the claims which follow.

We claim:

1. In a process for the production of alkylaluminoxane by the reaction of water and a trialkylaluminum compound in an organic solvent medium, wherein the improvement comprises conducting the reaction in the presence of an aluminoxane which functions as a reaction moderator.

2. A process as claimed in claim 1 wherein the trialkylaluminum is trimethylaluminum.

3. A process as claimed in claim 1 wherein the water and trialkylaluminum are reacted with one another in a two-stage reaction with the water to trialkylaluminum molar ratio being higher in the second state.

4. A process as claimed in claim 2 wherein the water and trialkylaluminum are reacted with one another in a two-stage reaction with the water to trialkylaluminum molar ratio being higher in the second state.

5. A process as claimed in claim 1 wherein the aluminoxane, which functions as a reaction moderator, is formed in situ during the initial stage of the process by the reaction of water, in highly diluted form, and trialkylaluminum.

6. A process as claimed in claim 2 wherein the preformed aluminoxane is formed in situ during the initial stage of the process by the reaction of water, in highly diluted form, and trialkylaluminum.

7. A process as claimed in claim 3 wherein the preformed alumioxane is formed in situ during the initial stage of the process by the reaction of water, in highly diluted form, and trialkylaluminum.

8. A process as claimed in claim 4 wherein the preformed aluminoxane is formed in situ during the initial stage of the process by the reaction of water, in highly diluted form, and trialkylaluminum.

9. A process as claimed in claim 1 wherein the water and trialkylaluminum are reacted with one another in a one-stage reaction with the water to trialkylaluminum molar being held substantially constant through the reaction until the desired final concentration of product is achieved.

10. A process as claimed in claim 2 wherein the water and trialkylaluminum are reacted with one another in a one-stage reaction with the water to trialkylaluminum molar being held substantially constant through the reaction until the desired final concentration of product is achieved.

* * * * *